United States Patent

Bui et al.

[11] Patent Number: 5,807,234
[45] Date of Patent: Sep. 15, 1998

[54] MYOSTIMULATOR CONTROL USING METABOLIC DEMAND AND MUSCLE PERFORMANCE

[75] Inventors: Tuan Bui, Green Oaks, Ill.; Stuart B. McConchie, Cambridge, United Kingdom; Peter A. Crosby, Bellevue, Wash.; Gordon Jacobs, Schweulisville, Pa.

[73] Assignee: Pacesetter, Inc., Sylmar, Calif.

[21] Appl. No.: 884,063

[22] Filed: Jun. 27, 1997

[51] Int. Cl.[6] ................................................ A61M 1/12
[52] U.S. Cl. ............................................................ 600/17
[58] Field of Search ............................ 600/16, 17; 607/17

[56] References Cited

U.S. PATENT DOCUMENTS 5,251,621  10/1993  Collins ........................................ 600/17
5,364,337  11/1994  Guiraudon et al. ........................ 600/16

Primary Examiner—William E. Kamm
Attorney, Agent, or Firm—Gottlieb, Rackman & Reisman

[57] ABSTRACT

In a cardiomyoplasty system, a rate responsive implantable device is disclosed which controls the stimulation of both the heart and a myoplasty muscle. The metabolic demand is used as a rate response parameter and one or both of the heart and the muscle stimulation are increased with metabolic demand. Under certain conditions, for example, if the muscle is tired, its stimulation is maintained constant or reduced and the cardiac stimulation is used to compensate for increased metabolic demand.

40 Claims, 6 Drawing Sheets

MYOSTIMULATOR CONTROL USING METABOLIC DEMAND AND MUSCLE PERFORMANCE

RELATED APPLICATIONS

The subject matter of the present application is related to commonly assigned co-pending U.S. application Ser. No. 08/659,580 filed Jun. 6, 1996, entitled CARDIOMYOPLASTY SIMULATOR WITH FEEDBACK CONTROL, now U.S. Pat. No. 5,693,000, incorporated herein by reference.

BACKGROUND OF THE INVENTION a. Field of Invention

This invention pertains to an implantable cardiac device for cardiac stimulation and for the stimulation of a skeletal muscle arranged and constructed to assist a patient's heart. More particularly, this invention pertains to a device which monitors the status of the muscle and the cardiac demand of the patient and controls the stimulation of the heart and the muscle in a manner which insures optimal haemodynamic operation available dependent on the status of the muscle.

b. Description of the Prior Art

Cardiomyoplasty is a procedure for treating mechanical failure of the heart, as a result of cardiac disease such as dilated cardiomyopathy, which results in inadequate cardiac output. Typically in the surgical procedure, the large skeletal muscle of the back, the latissimus dorsi, is dissected away from where it joins the spine, is inserted through an aperture made in the ribs, and wrapped around the heart muscle. A cardiomyoplasty stimulator electrically stimulates the latissimus dorsi muscle via a pair of fine wire electrodes threaded through the muscle. The muscle stimulations are timed to coincide with normal cardiac contractions, as determined from signals sensed via a conventional (either endocardial or epimyocardial) heart pacemaker lead system.

Cardiac output (i.e., the amount of blood pumped per unit time, usually measured in liters per minute) is the product of heart rate and stroke volume. Therefore, cardiac output can be adjusted by changing heart rate or by changing force of contraction, or both. In a conventional cardiomyoplasty system, the heart rate is the heart's own natural rate, and the stroke volume is augmented by the skeletal muscle assist. The amount of augmentation is controlled by the contraction of the muscle and its frequency. Typically, the skeletal muscle is stimulated at intervals which are typically an integer multiple of the cardiac pacing interval. In other words, the skeletal muscle may be stimulated for every second, third, fourth cardiac contraction.

One of the fundamental problems with the cardiomyoplasty procedure is that the force of contraction of the latissimus dorsi is unregulated. This may lead to insufficient force being generated, or conversely more force being generated than is needed. A collateral problem is that the skeletal muscle can fatigue, leading to its gradual degradation and loss of function. However, tiring the muscle may be avoided if the muscle is not delivering more force (work or power) than actually necessary. Therefore it is advantageous to measure the force generated by the muscle during each contraction, and to determine the beginning of fatigue state of the muscle, and use this information to regulate the strength of contraction, or the ratio of augmented cardiac cycles to unaugmented cycles, to allow the skeletal muscle time to rest and recover.

Previous inventions by Grandjean (see U.S. Pat. Nos. 5,098,442 and 5,067,960) have disclosed the use of intramuscular pressure or calorimetry to measure oxygen concentration in the muscle blood supply to determine fatigue in the muscle. While these systems may or may not work, they require a special lead with a sensor inserted into the skeletal muscle, with attendant problems of reliability and cost. Moreover, these references do not discuss metabolic demand.

It is well known from the work associated with electromyographic signals obtained from skeletal muscles that the characteristics of these signals change with the onset of fatigue, and can be determined by straight forward signal processing (see Basano, L., & Ottonello, P., "Real Time FFT to Monitor Muscle Fatigue", IEEE Trans on Biomed Eng, BME-33:1049–1051 1986, and Park, E, & Meek, S. G., "Fatigue Compensation of the Electromyographic Signal for Prosthetic Control and Force Estimation", IEEE Trans on Biomedical Engineering, 40: 1 0 October 1993). It appears that the most reliable predictor of the onset of fatigue in skeletal muscle based on the EMG is a change in the frequency spectrum (see Beliveau, L., van Hoecke, J., Garapon-Bar, C., Gaillard, E., Herry, J. P., & Bouissou, A. P., "Myoelectrical and Metabolic Changes in Muscle Fatigue", Int. J. Sports Med 13 (1992).

The relationship between muscle force and electromyogram for a latissimus dorsi muscle used for cardiac assistance was investigated by Cestari et al (Cestari, I. A., Moreira, L. F. P., Hayashida, S. A., Leimer, A. A., & Jatene, A. D., "Alternative Parameters for Evaluating the Performance of Skeletal Muscle in Cardiac Assistance", J. Cardiac Surg., 6:1 Supplement, 1991), and promising results were shown, but no modified myostimulation device or method of measurement was disclosed in this reference.

Methods and devices for determining muscle fatigue are disclosed in commonly assigned co-pending U.S. application Ser. No. 08/659,580 filed Jun. 6, 1996, entitled CARDIOMYOPLASTY SIMULATOR WITH FEEDBACK CONTROL, now U.S. Pat. No. 5,693,000, incorporated herein by reference. More particularly, this application discloses an apparatus and method for adjusting the output of a myostimulator by determining parameters of the skeletal muscle performance such as force, speed of contraction, or fatigue, via a standard lead by using a signal such as electromyogram or impedance variations in the muscle. While that invention is an improvement on previously disclosed systems, it does not link the muscle performance with cardiac performance or metabolic demand for optimal control of the system.

In previously disclosed cardiomyoplasty systems, the heart's own natural rhythm (as sensed by a conventional cardiac pacing lead system) is used to determine the rate of contraction. However, recognizing that patients undergoing the cardiomyoplasty procedure have very sick hearts, it may be wrong to assume that the heart's own natural rhythm is the optimal one to supply oxygenated blood needed for the body's metabolic demands.

OBJECTIVES AND SUMMARY OF THE INVENTION

It is an objective of this invention to use a conventional rate adaptive pacemaker system having a physiological sensor responsive to metabolic demand (e.g., minute ventilation) to overdrive the heart's natural rhythm (where necessary), and to additionally couple metabolic demand to the control of muscle force.

A further objective is to provide a cardiomyoplasty system in which haemodynamic operation is optimized by adjusting in synchrony the respective stimulations of the skeletal muscle and the patient's heart to the metabolic demand of the patient, to optimize the amount of skeletal muscle augmentation delivered to the need of the patient.

Briefly, an implantable cardiac device constructed in accordance with this invention includes two components: an electrical component consisting of a hermetic housing containing electronic control circuitry and a biological muscle wrapped around a heart, another portion of the cardiovascular system of a patient or otherwise arranged to provide cardiac assistance. The electronic component is coupled to the heart and to the muscle by electrodes for collecting information and for providing stimulation pulses thereto. The electronic component includes means for monitoring the condition of the muscle and means for adjusting both the muscle stimulation parameters and the cardiac pacing parameters in accordance with the muscle condition and the metabolic demand of the patient. Several modes of operation can be accomplished with the subject device depending on the condition of the patient, the general and current condition of the skeletal muscle, and so on. In one mode of operation, the pacing rate is changed responsive to the changes in the metabolic demand, while the myostimulation remains constant. In another mode of operation the myostimulation is changed responsive to the changes in metabolic demand while the pacing rate is maintained constant. In a third mode, pacing rate/myostimulation pairs are stored in a memory and retrieved, each pair being optimized for a particular metabolic demand.

Preferably metabolic demand is established by measuring the transthoracic impedance, using the electrodes associated with the pacing function. Alternatively the transthoracic impedance is measured using both the pacing and the myostimulation electrodes.

DETAILED DESCRIPTION OF THE PREFERRED EMBODIMENT

Figure 1:
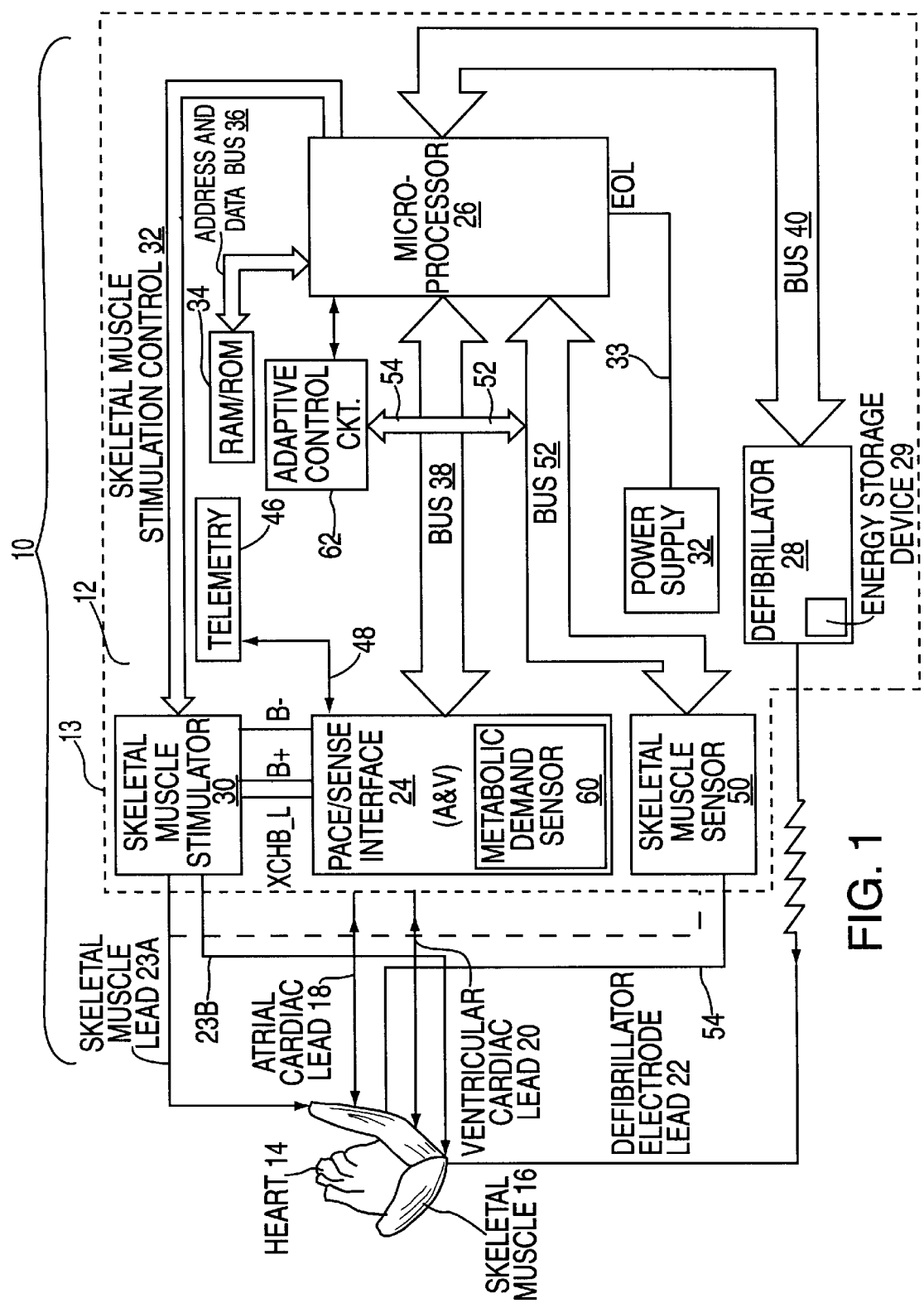
FIG. 1 shows a block diagram of an implantable cardiac device constructed in accordance with this invention.

In FIG. 1 there is depicted a block diagram of an implantable cardiac device 10. The device 10 is designed to be implanted within a patient and includes a hermetically sealed electronic module 12 having a hermetically sealed housing 13. The device 10 further includes a skeletal muscle 16 wrapped about the heart 14. It should be understood that the muscle may also be positioned about another organ of the cardiovascular system as well, or it may be shaped to form an independent, separate pump. Thus, the present invention is also applicable to aortal myoplasty and skeletal muscle ventricle.

Leads are also provided for connecting module 12 to a patient's heart 14 and skeletal muscle 16. These leads may include an atrial cardiac lead 18, a ventricular cardiac lead 20 extending to the atrium and the ventricle of the patient's heart 14, respectively, as well as a defibrillation electrode lead 22 and a pair of skeletal muscle lead 23A, 23B.

The pulse module 12 generally includes an analog/digital interface 24, a microprocessor 26, a defibrillator 28, a skeletal muscle stimulator 30 and a power supply 32. The interface 24 is provided for the detection of analog signals representing intrinsic atrial and ventricular activity and for the delivery of pacing pulses to the heart over leads 18 and 20. The microprocessor 26, in response to various inputs received from the interface 24 as well as from a defibrillator 16, performs various operations so as to generate different control and data outputs to module interface 24, skeletal muscle stimulator 30 and defibrillator 28. The power supply 32 provides reliable voltage to the other components of the pulse module. When the power supply 32 is nearly exhausted it generates an End-Of-Life (EOL) signal on line 33 to the microprocessor 26.

Skeletal muscle stimulator 30 generates electrical pulses on a skeletal muscle leads 23A, 23B for stimulating the skeletal muscle 16. Details of the manner in which the skeletal muscle stimulator operates can be found in U.S. Pat. No. 5,251,621 incorporated herein by reference. In addition, U.S. Pat. No. 5,632,716 discloses an apparatus and method of automatically training muscle 16.

The defibrillator 28 has an energy storage device 29 which may consist of one or more capacitors (not shown), and is used to produce high voltage pulses responsive to control signals from microprocessor 26 received on bus 40. The defibrillator electrode lead 22 transmits the defibrillator shocks from the implanted module 12 to the heart 14. The defibrillator 28 and its associated circuitry are optional and have been shown herein for the sake of completeness. A cardiomyostimulation system with defibrillation is shown in commonly assigned U.S. Pat. No. 5,500,004.

The microprocessor 26 is connected to a Random Access/Read Only memory unit 34 by an address and data bus 36. Unit 34 is used to store data and programming for microprocessor 26.

The module 12 also includes a telemetry circuit 46 over which control and data signals can be exchanged with the outside world. The telemetry circuit 46 is coupled to interface 24 by a bus 48.

Microprocessor 26 and interface 24 are connected by a data and communication bus 38 for exchanging various data.

The skeletal muscle stimulator 30 shown in FIG. 1, receives input signals from microprocessor 26 over the skeletal muscle stimulation control bus 32. In addition, the interface 24 supplies to stimulator 30 battery power for biphasic stimulation over two battery leads B+ and B– which provide energy for skeletal muscle stimulation. The battery leads B+, B– are floating with respect to the power supplied by supply 32 to provide signal isolation. Interface 24 receives a signal XCHB-L, which is a cross channel blanking control signal used to disable cardiac sensing by the interface 24 during generation of a skeletal muscle stimulation pulse. Therefore this signal prevents the microprocessor 26 from incorrectly classifying a skeletal muscle stimulation pulse as an episode of intrinsic cardiac activity. Details of the skeletal muscle stimulator and interface 24 are provided in commonly assigned U.S. Pat. No. 5,251,621, incorporated herein by reference.

Importantly, module 12 further includes a skeletal muscle sensor 50. The sensor 50 is connected to microprocessor 16 by a bus 52, and to muscle 16, either through leads 23a, 23b or, if necessary by an electrode 54. The purpose of the sensor 50 is to determine the condition of the muscle 16, i.e., whether the muscle 16 is still not fully trained and needs further training, or the muscle is over- or under excited, or the muscle is tired. The muscle condition information is sent to the microprocessor via bus 52, which in response modifies its commands to the muscle stimulator 30, and, if required, to interface 24.

More specifically, as discussed in the above-mentioned U.S. application Ser. No. 08/659,580, now U.S. Pat. No. 5,693,000, sensor 50 is used for monitoring muscle performance using a detector such as electromyogram or intramuscular impedance are used to develop a signal with a relationship to the muscle performance parameter being measured. The detector signals are used to affect the operation of the myostimulation timing and control circuits implemented in the microprocessor 26. If the muscle 16 was determined to be suffering from fatigue, then the ratio of augmented to unaugmented cardiac cycles can be changed to reduce the work load on the cardiac muscle. (Physiologically, the patient would start to feel tired due to the reduction in cardiac output and therefore reduce his/her activity level, thereby reducing the demand on the heart, and thus closing the control loop). The operation of the controlling algorithm for the cardiomyoplasty stimulating system can be altered with an external programmer (not shown) communicating with the implanted pacer 12 via telemetry circuit 46.

The pacer 12 further includes a metabolic demand sensor 60, shown in FIG. 1 as being incorporated into the interface 24, and generating a metabolic parameter (MP) indicative of the metabolic demand of the patient. The metabolic demand sensor may be any sensor which can generate a signal indicative of the metabolic demand of the patient. In this application, the term 'metabolic demand sensor', is used generically to cover not only sensors measuring a metabolic parameter such as transthoracic impedance, QT interval, blood temperature, evoked potential, oxygen saturation, right ventricular pressure, and so on, but also sensors indicative of the patient's physical activity, such as the output of a piezoelectric accelerometer. Future developments in implantable biosensors may result in other control parameters such as concentration of one or more biochemical species.

In addition, the pacer 12 is provided with an adaptive control circuit 62 in communication with the muscle sensor 50 via bus 52 and the microprocessor 26. The purpose of the control circuit 62 is to monitor the status of the muscle 16 as determined by sensor 50 and to coordinate its stimulation with the cardiac stimulation, i.e., the pacing signals generated by the interface 24.

Figure 2:
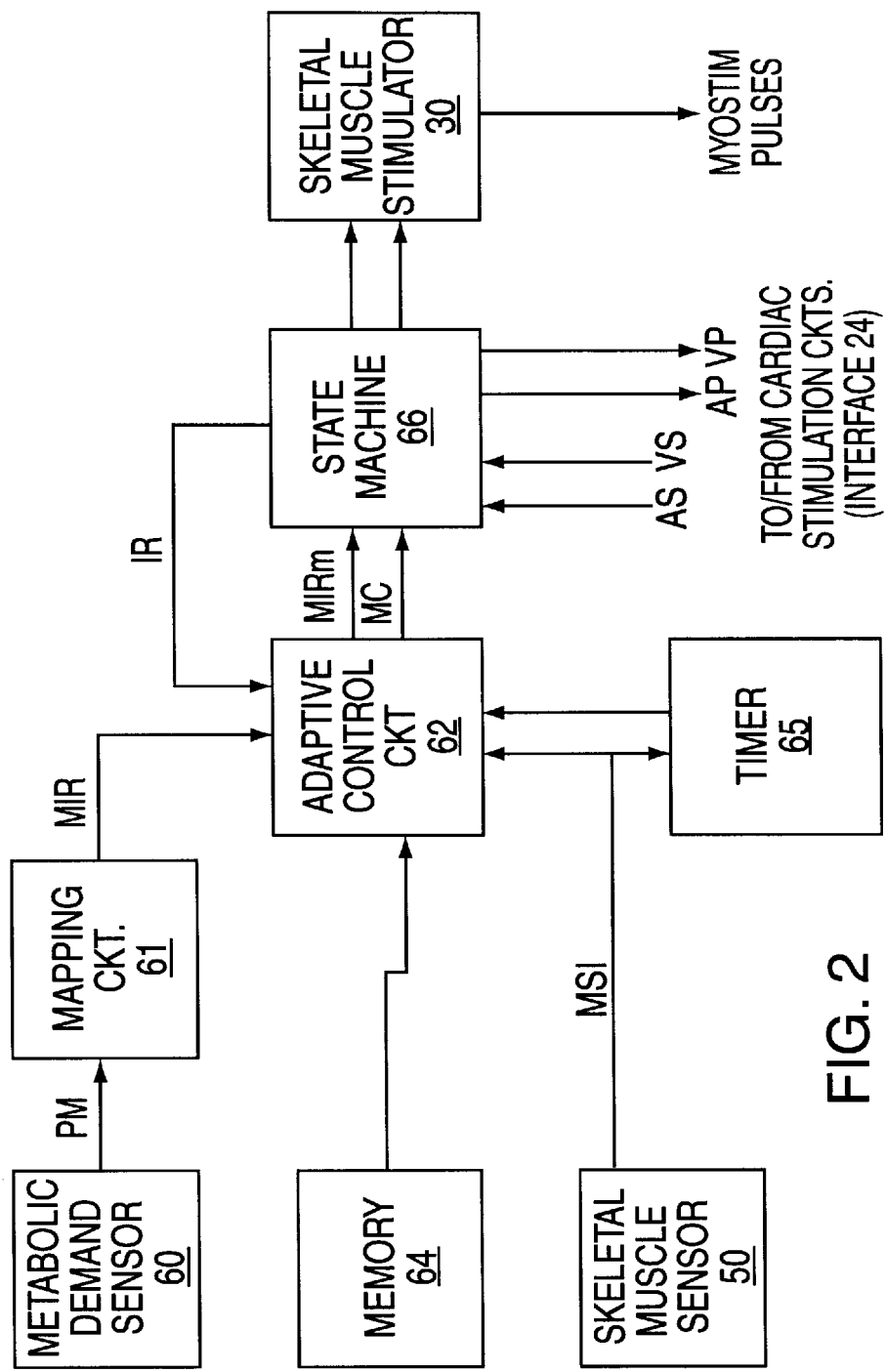
FIG. 2 shows a block diagram for the components of the cardiac device of FIG. 1 used for controlling synchronous pacing and muscle stimulation functions.

A block diagram of how circuit 62 and other circuits used for generating pacing and muscle stimulating signals are shown in FIG. 2. In this Figure, the metabolic parameter (MP) from the metabolic demand sensor 60 is fed to a mapping circuit 61. This circuit 61 is used for conformal mapping the metabolic parameter into a corresponding Metabolic Indicated Rate (MIR) using a rate response function. This latter process is well known in the art and need not be described (see for instance U.S. Pat. No. 5,487,753).

A muscle status indication (MSI) from sensor 50 and the MIR signal are fed to the adaptive control circuit 62. This circuit 62 is also associated with a memory 64, which may be, for example, a look-up table. A timer 65 is also provided to measure the length of time during which muscle 16 is tired, as discussed below.

The circuit 62 generates corresponding metabolic pacing (MIRm) and myostimulation (MC) control parameters to a state machine 66. It should be understood that circuits 61 and 62 and state machine 66, as well as all or part of the sensors 50 and 60 may be implemented as software in the microprocessor 26, however they are indicated herein as discrete components for the sake of clarity.

If pacer 12 is a dual chamber pacer, then the state machine 66 also receives an atrial sense signal (AS) and a ventricular sense signal (VS) from the interface 24. In response to these signals the state machine generates on demand atrial (AP) and ventricular (VP) pacing commands to the cardiac (i.e. atrial and ventricular) stimulation circuits in interface 24 which then generate corresponding analog pacing pulses to the appropriate cardiac chambers. A state machine for a dual chamber pacer which may be adapted to perform the functions described herein is disclosed for example in U.S. Pat. No. 5,441,523.

In addition, the state machine also sends a stimulation interval (SI) command and a stimulation duration (SD) command to the muscle stimulator 30. The stimulator 30 generates stimulation pulses to the skeletal muscle 16, as described more fully below.

Finally, the state machine 66 also generates an intrinsic rate (IR) signal to the adaptive control circuit 62.

The circuits of FIG. 2 can be programmed to operate in a number of different modes, dependent on a number of different factors, such as the cardiac condition of the patient, the status of the skeletal muscle and so on. For example, if the patient is suffering from bradycardia, it may be clinically advantageous to maintain the heart rate of the patient constant, or at least, minimize extreme heart rate variations. For this mode, while the rate MIR changes in accordance with the metabolic demand of the patient, the parameter MIRm is kept substantially constant (as compared to a parameter without myostimulation), and any increase or decrease in the metabolic demand is met by increasing or decreasing the myostimulation level, i.e., by changing the MC signals to the state machine 66.

In another mode, for example when the skeletal muscle is tired, it is more advantageous if the myostimulation level is kept constant or decrease and the cardiac stimulator is changed to conform to the changes in the metabolic demand, for example by changing MIRm.

In general, it is expected that MIRm is somewhat lower than the corresponding MIR because MIR is normally determined by the mapping circuit 61 without taking myostimulation into consideration.

In yet another mode of operation, the memory 64 is used to store pairs of MIRm and MC control parameters, each pair corresponding to and being optimized for a particular level of metabolic demand. These pairs may be determined empirically by the clinician after implantation. In this mode, the MIR parameter or the MP parameter are used directly as an indicia of metabolic demand. This indicia is then used to look up a corresponding pair j of control parameters $MIRm_j$, $MSC_j$, in memory 64.

A more complex mode of operation of the circuits of FIG. 2 shall now be described which is a combination of all the simpler modes described above, in conjunction with the flow chart of FIGS. 3a and 3b. In this complex mode, the control circuit 62 adapts itself dynamically to the changes in the metabolic demand and skeletal mode status.

Initially, the system operates in a constant cardiac pacing mode, i.e. a mode wherein changes in the metabolic demand are satisfied by the skeletal muscle. The system is initiated in step 100 when the pacemaker 12 is implanted. In step 102 the controller circuit 62 obtains the current metabolic indicated rate (MIR) from circuit 61, as well as a muscle status indication (MSI) and a current intrinsic rate (IR). In step 104, the controller circuit 62 uses these parameters to look up a corresponding myostimulation control parameter (MC) in memory 64. These parameters are either stored in the memory 64 by the manufacturer, or are provided by the clinician at implantation or during a follow-up visit. The adaptive control circuit 62 then sends these parameters MIRm and MC to state machine 66.

In step 106, the state machine 66 receives these parameters and generates corresponding pacing and myostimulation signals (AP, VP, SI and SD). The rules for generating these signals stored in memory 34 (FIG. 1).

Figure 4:
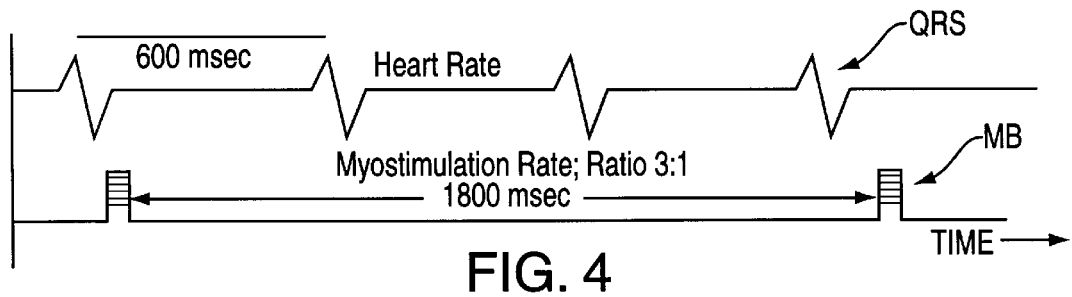
FIG. 4 shows a typical heartbeat and associated myostimulation bursts.

Typical cardiac events such as standard QRS complexes are shown in FIG. 4, together with standard myostimulation bursts MB. In this Figure, the parameter MIRm is 100 ppm. Therefore the interval between the QRS complexes is 600 msec. Initially, based on information received from memory 64 and the corresponding myostimulation control signal from the circuit 62, the state machine defines a stimulation interval (SI) of 1800 msec. Alternatively, the state machine 66 may define to the muscle stimulator 30 a myostimulation ratio, such as 3:1. This ratio indicates that the skeletal muscle 16 is simulated after every third QRS complex.

Figure 5:
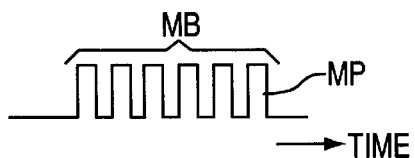
FIG. 5 shows the individual pulses of one of the myostimulation bursts of FIG. 4.

FIG. 5 shows details of a typical myostimulation burst MB as being composed of six rectangular myostimulation pulses MP.

Figure 3A:
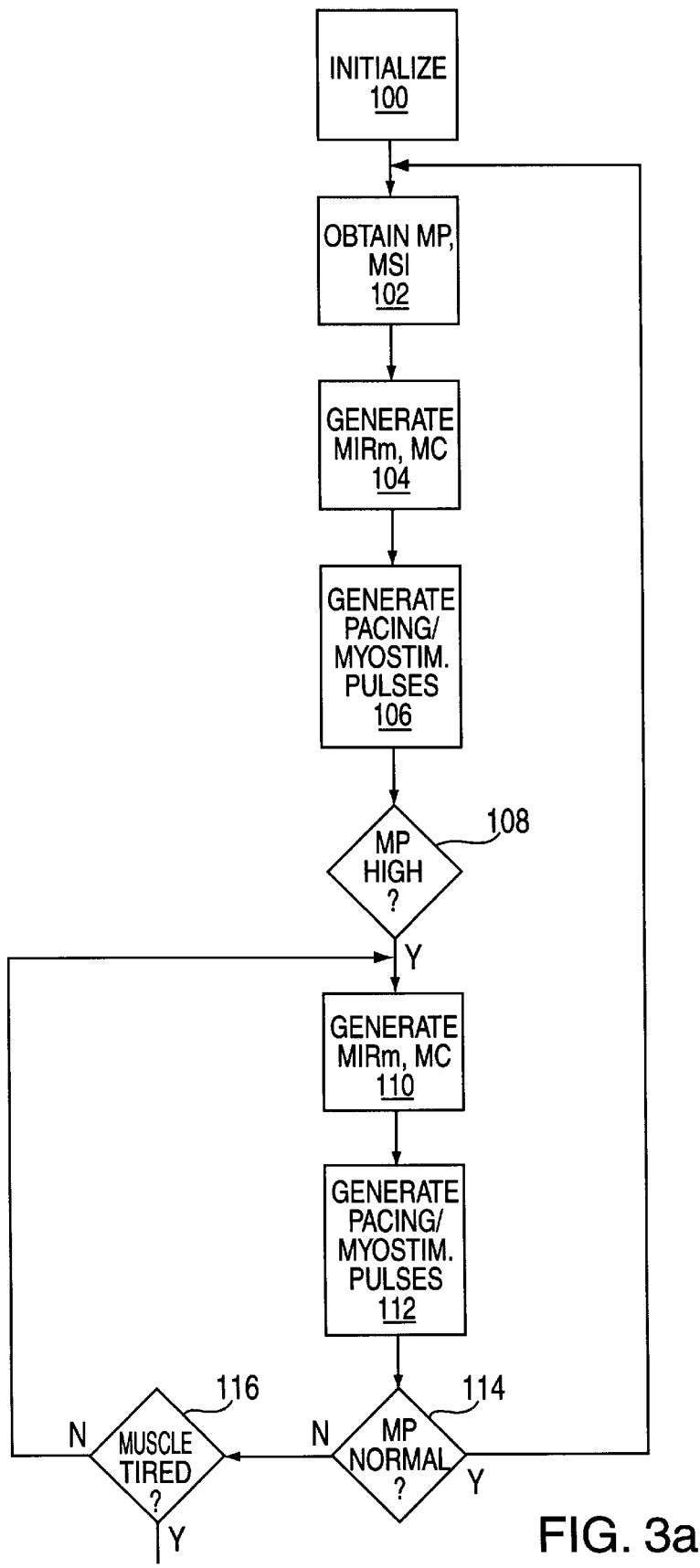
FIGS. 3a and 3b show a flow chart for the operation of the cardiac device of FIGS. 1 and 2.
Figure 3B:
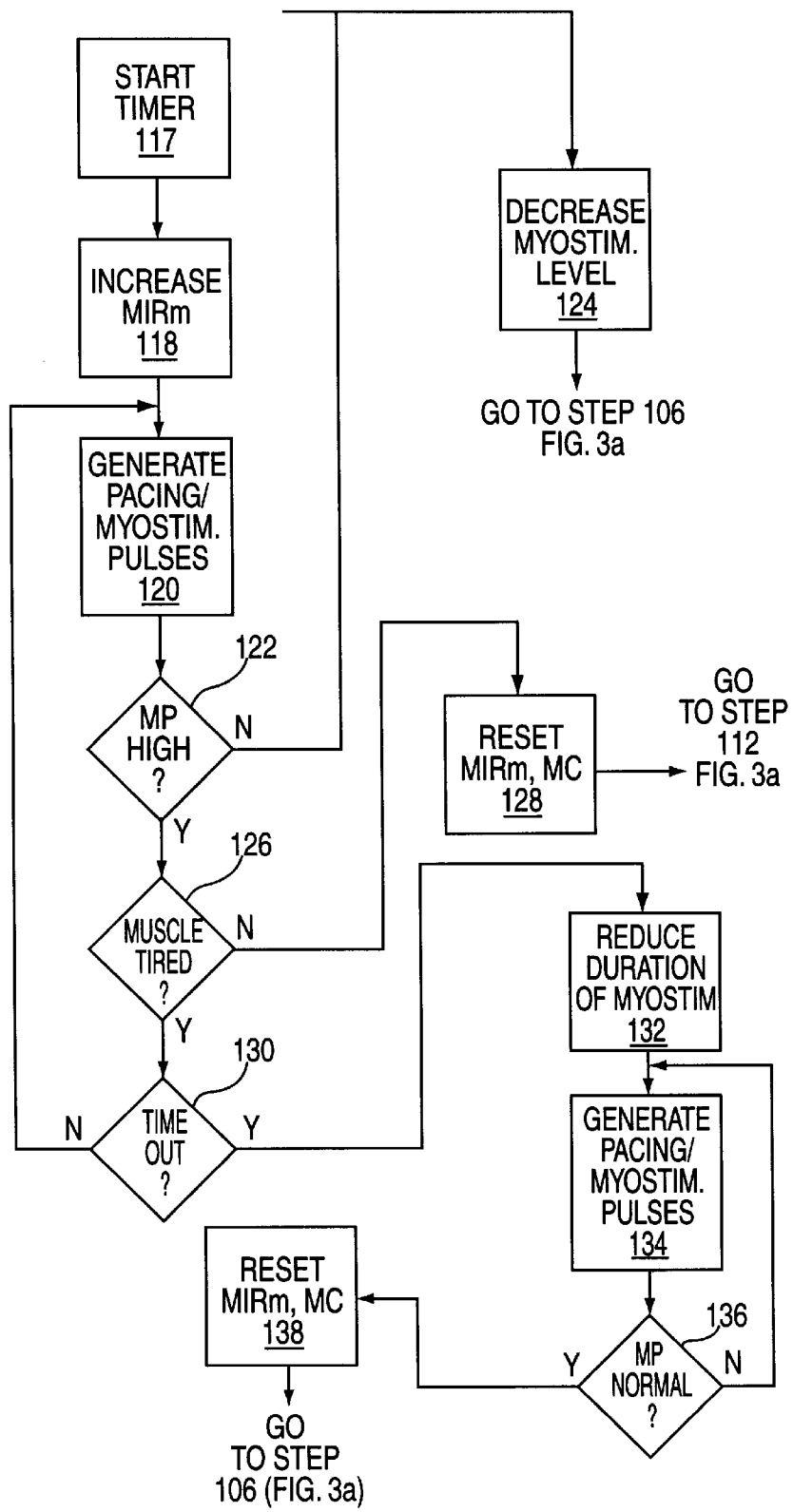

Getting back to FIG. 3a, following step 106, in step 108 a check is performed as to whether the metabolic parameter MP has changed. If it has not, then the system loops back to step 104.

Figure 6:
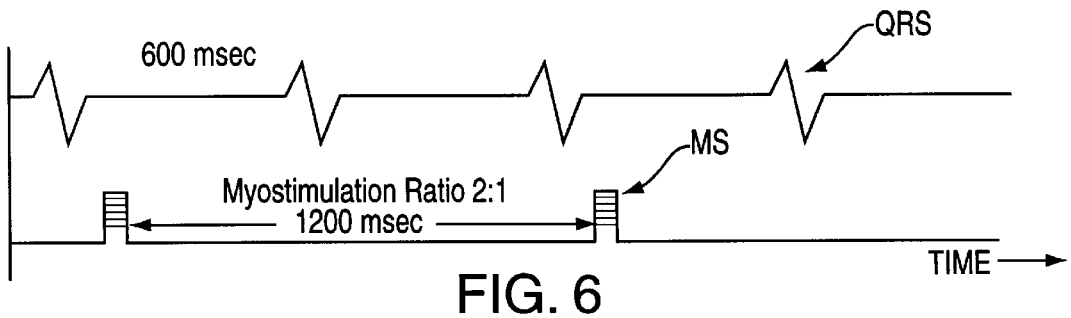
FIG. 6 shows the heartbeat and myostimulation bursts during high metabolic demand in accordance with this invention.

If in step 108 it is determined that MP has increased, indicating, for example, a prolonged exercise period, then in step 110 a new parameter MC is generated and provided to state machine 66. More specifically, in this mode, MC is modified to compensate for the increase in metabolic demand while MIRm remains unchanged or increased only slightly. The state machine then generates pacing/myostimulation signals corresponding to these latter set parameters. For example, as shown in FIG. 6, the output (i.e. the volume of pumped blood) of the system is increased by decreasing the myostimulation ratio from 3:1 to 2:1. Normally, i.e., in a standard pacemaker without myostimulation, an increase in metabolic demand results in an increase in the MIR parameter. Thus, the MIR with a higher physical activity level, MIR may increase from 100 ppm to 120 ppm. However in the present invention, the parameter MIRm is maintained by control circuit 62 at the same level as in FIG. 5, i.e. at 100 ppm, or as shown in FIG. 6, it is increased slightly to 110 ppm. This is especially important for a patient suffering from bradycardia.

In step 114 a check is performed to determine if the metabolic demand parameter MP is normal. If it is, then the nominal values for the MIRm and MC are generated in step 104, and the system returns to normal, low physical activity, operation.

If in step 114 it is determined that MP is still high, then in step 116 a check is performed by the control circuit 62 to determine if the skeletal muscle is tired. If the muscle is not tired then the state machine 66 continues to generate the commands necessary to produce the pacing/myo-stimulation process shown in FIG. 6.

Figure 7:
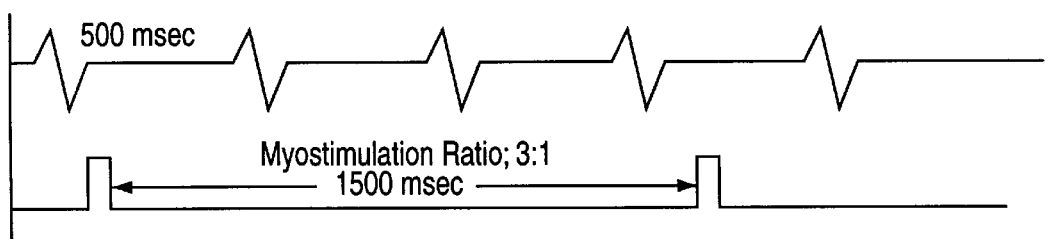
FIG. 7 shows the heartbeat and the myostimulation bursts during high metabolic demand with the muscle being fatigued.

If the muscle 16 is found to be tired in step 116, then in step 117 (FIG. 3b) a timer 65 is started. Next, in step 118 MIRm is increased for example to 120 ppm, and the MC is adjusted to request a myostimulation ratio of 3:1. In step 120 the pacing/myostimulation signals for this sequence are generate resulting in the stimulation profile shown in FIG. 7.

In step 122 the MP is checked to determine if the metabolic demand is still high. If it is not, then in step 124 MIRm is reduced to a lower level corresponding to the metabolic demand indicated by the MP parameter. Normal pacing/stimulation is resumed (step 106, FIG. 3) and the timer 65 is reset.

If in step 122 the MP still indicates a high level of physical activity then in step 124 a check is made to determine if the muscle 16 is still tired. If the muscle 16 is not tired anymore than the MIRm is reset to its lower value of 100 or 110 ppm, the myostimulation ratio is reset to its lower value (2:1) (step 128), the pacing/myostimulation for the sequence of FIG. 6 is resumed (step 112, FIG. 3a) and the timer 65 is reset.

Figure 8:
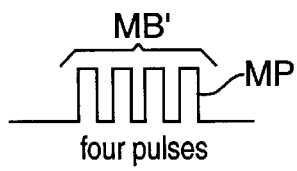
FIG. 8 shows the individual pulses for the myostimulation bursts of FIG. 7.

If in step 126 the muscle is still tired, then in step 130 the timer 65 is checked to see if a certain preselected time has elapsed. This time duration is selected to allow the muscle 16 to recuperate and may be 1 min.–1 hour. If this time duration exceeds a preset value, the muscle 16 has not recuperated then its workload is reduced even further. More specifically in step 132 the myostimulation control parameter MC is adjusted to reduce the duration, i.e. the number of pulses per myostimulation burst MB, for example from six to four, as shown in FIG. 8. Alternatively, the energy delivered by muscle 16 can be reduced by other means. For example, this may be accomplished by reducing the amplitude of the muscle stimulation pulses, i.e., from 5 v to 2 v. Another alternative is to increase the frequency of the bursts, i.e., from 35 Hz to 85 Hz. In step 134 the commands necessary to obtain this new sequence are generated by state machine 66.

In step 136 the metabolic parameter is checked again. If it has returned to normal, then in step 138 the parameters MIRm and MC are reset to the levels of step 104 and normal operation resumes (step 106).

If in step 136 MP has not returned to normal then the operation as last defined in step 134 continues. Thus during steps 134, 136, the work load on the muscle is reduced not only increasing the interval between the myostimulation bursts but also by decreasing the number of stimulations in each burst.

A preferred means for determining the metabolic demand is by measuring the transthoracic impedance or, more correctly, changes in transthoracic impedance. This parameter has been found to be proportional to tidal volume, and the tidal volume signal when multiplied by respiration rate (derived from the transthoracic impedance signal) yields minute ventilation.

Conventionally, in a heart pacemaker system, transthoracic impedance is measured by injecting a small current pulse between the ring electrode of a bipolar ventricular lead system and the pacemaker housing which is usually placed in a surgically made pocket in the left or right pre-pectoral region. The voltage generated by this current pulse is conventionally measured between the tip electrode of the lead system and the pacemaker can. Details of this method of determining minute volume are found in commonly assigned U.S. Pat. No. 4,901,725. The same method can be used in this invention.

In an alternative embodiment, and particularly in the case where the size of the housing 13 or the surgical procedure may require that the pacer 12 be disposed in the abdomen instead of the pre-pectoral region, one or more of the muscle stimulation electrodes (23A, 23B) can be used as a common electrode for the purposes of measuring trans-thoracic impedance. In this embodiment, electrical switches inside the muscle stimulation circuits and the transthoracic impedance measurement circuits are used to route the appropriate signals to the electrodes used in the measurement.

Figure 9:
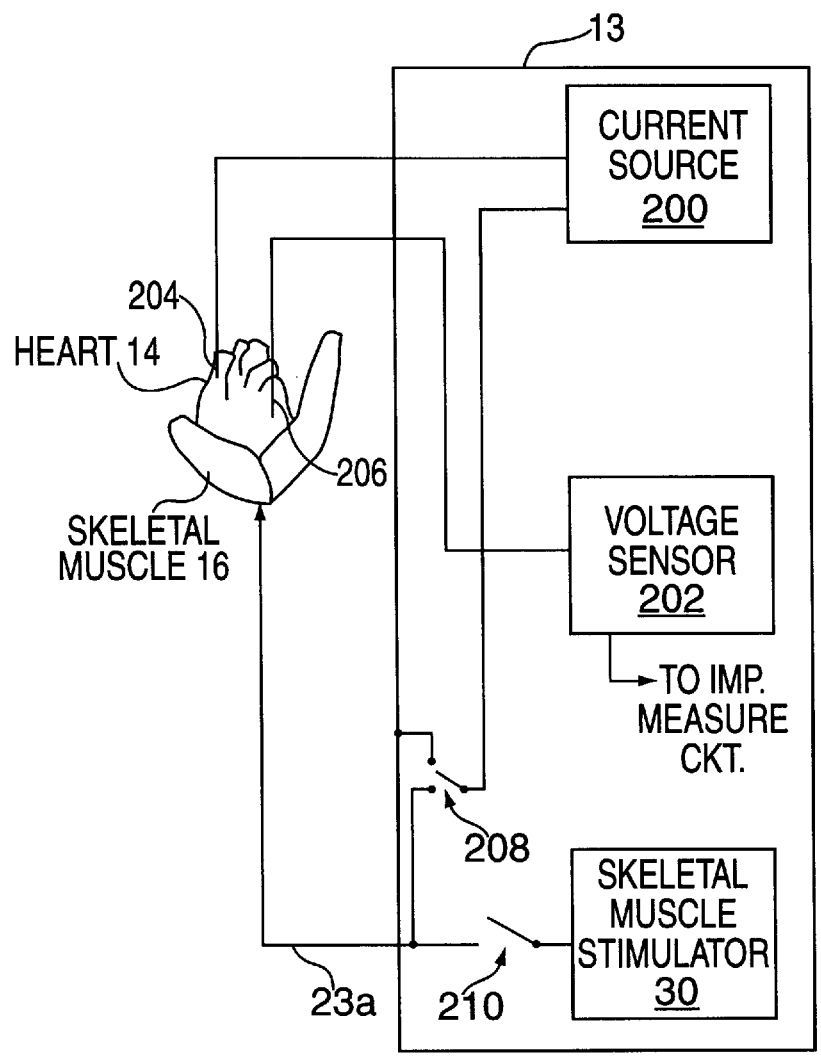
FIG. 9 shows a circuit for determining minute volume in accordance with this invention.

More particularly, as shown in FIG. 9, the metabolic demand sensor 60, in accordance with the present embodiment, includes a current pulse generator 200 and a voltage sensor 202. The current pulse generator is connected to a wire of, for example, lead 18 terminating in a ring electrode 204. The voltage sensor 202 is connected to a tip electrode 206 of a second wire belonging to the same lead 18 or to lead 20. A switch 208 is used to connect both generator 200 and sensor 202 either to the housing 13 or to one of the stimulator leads such as lead 23A. A second switch 210 is used to isolate the lead 23A from the skeletal muscle stimulator 50 during the impedance measurement. For this embodiment, the switch 208 connects to the lead 23A. Therefore the current pulse from generator 200 flows through the lead 18 to the ring electrode 204 and returns through the stimulator lead 23A. The voltage induced by this current between the tip electrode 206 and the lead 23A is then detected by sensor 202 and transmitted to an impedance measurement circuit (not shown).

Other electrode combinations are possible to determine both the transthoracic impedance signal or the signals used to determine muscle status and performance and appropriate switches are provided inside the circuits to route measurements signals to the desired place at the desired time. The choice of best electrode combination for measuring minute ventilation can be deferred until after implant because the switches are externally programmable via the telemetry link.

In all the described embodiments, one or more of the parameters used to control the device can be programmed externally via the telemetry link through telemetry circuit 46. In addition, the telemetry link can be used to telemeter out to the programmer one or more parameters recorded and stored in the device.

U.S. Pat. No. 5,500,004, discloses a combined myostimulation and implantable cardiac defibrillator to treat both the poor cardiac output as well as potentially lethal tachyarrhythmias known to be common with the underlying disease of cardiomyopathy. The invention disclosed here could also be included in a combined device to provide augmentation of contraction (stroke volume), delivery of anti-arrhythmia electrical therapy, and pacing to control heart rate in response to the body's metabolic demand.

Moreover, while a dual chamber pacer 12 is described, the subject invention is equally applicable to a single chamber device.

Although the invention was described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A control device for stimulating a patient's heart and a muscle arranged to augment cardiac function, said control device comprising:

a cardiac sensor for sensing intrinsic activity in said heart and generating in response cardiac sensed signals a pace generator for generating pacing signals to said heart in response to pacing commands;

a muscle generator for generating stimulation signals to said muscle in response to stimulation commands;

a metabolic demand sensor for determining a metabolic demand of said patient and generating a metabolic demand parameter; and a controller receiving said cardiac sensed signals and said metabolic demand parameter and generating in response said pacing and said stimulation commands.

2. The device of claim 1 wherein said controller changes said stimulation commands in response to changes in said metabolic demand parameter while keeping said pacing commands substantially constant.

3. The device of claim 1 wherein said controller changes said pacing commands in response to changes in said metabolic parameter while keeping said stimulation signals substantially constant.

4. The device of claim 1 wherein said controller includes a memory holding a plurality of pacing and stimulation commands and a selector for selecting one of said pacing and one of said stimulation commands in response to said metabolic demand parameter.

5. The device of claim 1 further comprising a muscle sensor for sensing a status of said muscle and generating corresponding muscle status signals.

6. The device of claim 5 wherein said controller receives said muscle status signals and generates one of said stimulation and pacing commands in response to said muscle status signals.

7. An implantable cardiac device for stimulating on demand a patient's heart and a muscle arranged and constructed to assist said heart, said device comprising:

a cardiac sensor for sensing intrinsic activity in said heart and generating corresponding sensed cardiac signals;

a pace generator for generating pacing signals for said heart in response to pacing commands;

a muscle generator for generating stimulation signals to said muscle in response to stimulation commands;

a muscle sensor for generating a status of said muscle and generating in response sensed muscle signals; and a controller receiving said sensed cardiac signals and said sensed muscle signals and generating in response said pacing and said stimulation signals, synchronously.

8. The device of claim 7 wherein sensed muscle signals include a first signal indicative of a normal muscle status and a second muscle signal indicative of a tired muscle status and said controller has a first mode of operation corresponding to said first signal and a second mode of operation corresponding to said second signal.

9. The device of claim 8 wherein said controller generates first stimulation signals to define a first energy level in said fast mode and second stimulation signals defining a second energy level lower than said first energy level.

10. The device of claim 8 wherein said muscle generator generates said stimulation pulses at a stimulation rate.

11. The device of claim 10 wherein said controller defines a first stimulation rate in response to said first signal and a second stimulation rate in response to said second signal, said first stimulation rate being higher than said second stimulation rate.

12. The device of claim 8 wherein said muscle generator generates stimulation pulses having a duration defined by said controller.

13. The device of claim 12 wherein said controller generates a first duration consisting of a first number of pulses in response to said first signal and a second duration consisting of a second number of pulses in response to said second signal, said first number being higher than said second number.

14. The device of claim 7 further comprising a demand sensor for sensing a metabolic demand of said patient and generating a demand parameter, said controller receiving said demand parameter for generating at least one of said pacing and stimulation commands.

15. The device of claim 14 wherein said pacing generator generates said pacing pulses at a pacing rate defined by said pacing command and said muscle generator generates stimulation pulses at a stimulation rate defined by said stimulation command.

16. The device of claim 15 wherein said controller increases at least one of said pacing rate and said stimulation rate when said demand parameter indicates an increase in said metabolic demand.

17. The device of claim 16 wherein said pacing rate is increased with the increase in said metabolic demand while said stimulation command remains constant.

18. The device of claim 17 further comprising a selector for selecting for each demand parameter a corresponding pacing and stimulation command.

19. The device of claim 18 further comprising a memory for storing a pluralist of pacing and stimulation commands, said selector retrieving said corresponding pacing and stimulation commands from said memory.

20. The device of claim 16 wherein said stimulation rate is increased with the increase in said metabolic demand while said pacing rate remains constant.

21. An implantable cardiac device for controlling the simultaneous stimulation of a patient's heart and a muscle constructed and arranged to augment the patient's cardiac function, said device comprising:
a pacing generator for generating pacing pulses for said heart in response to pacing commands;
a muscle stimulator for generating stimulation pulses for said muscle in response to stimulation commands;
a demand sensor for sensing a metabolic demand of said patient and generating a corresponding demand parameter; and
a controller receiving said metabolic demand and selecting said pacing and stimulation commands to increase said cardiac function when said metabolic demand increases.

22. The device of claim 21 wherein said controller selects said pacing command to increase blood flow in response to an increased metabolic demand by increasing a pacing rate of said heart.

23. The device if claim 22 wherein said controller selects said stimulation command to increase blood flow in response to an increased metabolic demand by increasing the effect the stimulation of said muscle.

24. The device if claim 22 wherein said controller selects said stimulation command to increase blood flow in response to an increased metabolic demand by increasing said stimulation rate.

25. The device of claim 21 further comprising a muscle sensor for sensing a status of said muscle and generating in response a muscle sense signal.

26. The device of claim 25 wherein said controller has a first mode of operation corresponding to a low metabolic demand and a second mode of operation corresponding to a high metabolic demand, and wherein in said second mode, said controller increases the stimulation of said muscle as compared to said first mode.

27. The device of claim 26 wherein said controller has a third mode of operation responsive to a muscle sense signal indicative of a tired muscle status, wherein in said third mode, the stimulation of said muscle is decreased as compared to said second mode and the pacing of said heart is increased.

28. The device of claim 27 wherein said third mode is maintained in the presence of the tired muscle status as indicated by said muscle sense signal.

29. A method of simultaneously stimulating a heart and a muscle constructed and arranged to augment cardiac functions in a patient by using an implantable device, said method comprising the steps of:
generating pacing pulses to the heart at a pacing rate;
generating stimulation pulses to the muscle at a stimulation rate;
sensing a metabolic demand of said patient; and
increasing the stimulation of one of heart and muscle if said metabolic demand increases while maintaining the stimulation of the other of said heart and muscle substantially constant.

30. The method of claim 29 wherein the stimulation of said heart is increased by increasing said pacing rate.

31. The method of claim 29 wherein the stimulation of said muscle is increased.

32. The method of claim 31 wherein the stimulation of said muscle is increased by increasing said stimulation rate.

33. The method of claim 32 further comprising the step of sensing if said muscle is tired.

34. The method of claim 33 further comprising increasing the pacing rate and decreasing said stimulation rate if said muscle is tired.

35. The method of claim 33 further comprising the step of decreasing a duration of the stimulation pulses.

36. An implantable cardiac device for controlling the simultaneous stimulation of a patient's heart and a muscle constructed and arranged to augment the patient's cardiac function, said device comprising:
a cardiac sensor for sensing intrinsic activity in said heart and generating cardiac sensed signals;
a pacing generator for generating pacing pulses for said heart in response to pacing commands;
a muscle stimulator for generating stimulation pulses for said muscle in response to stimulation commands;
a muscle sensor for sensing a status of the muscle and generating muscle status signals;
a cardiac lead associated with said cardiac sensor and extending to said heart;
a myostimulation lead associated with one of said muscle stimulator and said muscle sensor and extending from said muscle stimulator to said muscle;
a demand detector for sensing a metabolic demand of said patient and generating a corresponding demand parameter, said metabolic demand parameter being generated using said myostimulation lead; and
a controller receiving said cardiac sensed signals, said muscle status signals and said metabolic demand and selecting said pacing and stimulation commands to increase said cardiac function when said metabolic demand increases.

37. The device of claim 36 wherein said demand detector detects a minute volume.

38. The device of claim 36 wherein said demand detector detects said metabolic demand parameter based on a transthoracic impedance.

39. The device of claim 36 wherein said demand detector includes a current generator for generating a current through one of said leads and a voltage sensor for sensing a voltage through the other of said leads, said transthoracic impedance being dependent on said current and said voltage.

40. The device of claim 39 further comprising a switch for switching one of said leads from said demand detector to one of said cardiac and muscle sensors.

* * * * *